United States Patent
Waller et al.

(10) Patent No.: US 7,906,351 B2
(45) Date of Patent: Mar. 15, 2011

(54) METHOD FOR METAL GATE QUALITY CHARACTERIZATION

(75) Inventors: James Lynn Waller, McKinney, TX (US); Vladimir Y. Zhukov, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 75 days.

(21) Appl. No.: 12/537,296

(22) Filed: Aug. 7, 2009

(65) Prior Publication Data

US 2010/0035369 A1 Feb. 11, 2010

Related U.S. Application Data

(60) Provisional application No. 61/086,872, filed on Aug. 7, 2008.

(51) Int. Cl.
*H01L 21/66* (2006.01)
*H01L 21/336* (2006.01)

(52) U.S. Cl. ...... 438/16; 438/197; 438/592; 257/E21.53; 257/E21.622

(58) Field of Classification Search ............ 438/14, 438/16, 197, 275, 592; 257/E21.529, E21.53, 257/E21.622
See application file for complete search history.

(56) References Cited

U.S. PATENT DOCUMENTS

| | | | | |
|---|---|---|---|---|
| 6,853,143 B2 * | 2/2005 | Nakasuji et al. | ......... | 315/111.81 |
| 7,232,997 B2 * | 6/2007 | Edinger et al. | ................ | 250/311 |
| 7,727,842 B2 * | 6/2010 | Mehrad et al. | ................ | 438/275 |
| 7,816,213 B2 * | 10/2010 | Matsuki | ........................ | 438/283 |
| 2009/0053883 A1 * | 2/2009 | Colombo et al. | ............. | 438/592 |
| 2009/0232385 A1 * | 9/2009 | Matsuoka et al. | ............. | 382/145 |

* cited by examiner

*Primary Examiner* — Tuan N. Quach

(74) *Attorney, Agent, or Firm* — Jacqueline J. Garner; Wade J. Brady, III; Frederick J. Telecky, Jr.

(57) ABSTRACT

Measuring the amount of unreacted polysilicon gate material in a fully silicided (FUSI) nickel silicide gate process for metal oxide semiconductor (MOS) transistors in an integrated circuit (IC) to guide process development and monitor IC production requires a statistically significant sample size and an economical procedure. A method is disclosed which includes a novel deprocessing sequence of oxidizing the nickel followed by removing the nickel silicide by acid etching, acquiring an SEM image of a deprocessed area encompassing a multitude of gates, forming a quantifiable mask of the original gate area in the SEM image, forming a quantifiable image of the unreacted polysilicon area in the SEM image, and computing a fraction of unreacted polysilicon.

18 Claims, 6 Drawing Sheets

METHOD FOR METAL GATE QUALITY CHARACTERIZATION

FIELD OF THE INVENTION

This invention relates to the field of integrated circuits. More particularly, this invention relates to integrated circuits with metal silicide gates.

BACKGROUND OF THE INVENTION

Integrated circuits (ICs) featuring metal oxide semiconductor (MOS) transistors fabricated at the 45 nm technology node may include fully silicided (FUSI) gates, which start with polycrystalline silicon (polysilicon) gates and react the polysilicon with a covering layer of nickel metal to form nickel silicide gates. FUSI gates offer performance advantages compared to polysilicon gates capped with silicide. Fabrication processes to produce FUSI gates are problematic, often resulting in scattered regions of unreacted polysilicon in gates. Improvement of FUSI processes and maintaining acceptable yields in IC manufacturing facilities requires accurate and economical assessment of the fraction of unreacted polysilicon gate material in an IC with FUSI gates. Commonly methods of measuring the fraction of unreacted polysilicon gate material include transmission electron microscopy (TEM). TEM has limited throughput and sample size, such that providing a statistically reliable sample is economically prohibitive.

SUMMARY OF THE INVENTION

This Summary is provided to comply with 37 C.F.R. §1.73, requiring a summary of the invention briefly indicating the nature and substance of the invention. It is submitted with the understanding that it will not be used to interpret or limit the scope or meaning of the claims.

The instant invention provides a method of measuring a fraction of unreacted polycrystalline silicon (polysilicon) in an integrated circuit (IC) with fully silicided (FUSI) gates on a statistically significant sample is addressed by the instant invention, by a process sequence including deprocessing an IC in a novel manner to expose any unreacted polysilicon, acquiring an image of a statistically significant sample region using scanning electron microscopy (SEM), generating a mask image from the SEM sample image which identifies all gate regions in the SEM sample image, applying the mask image to the SEM sample image to produce a masked image of gate regions with unreacted polysilicon, manipulating the masked image to facilitate quantification of the gate regions with unreacted polysilicon, measuring the amount of area with unreacted polysilicon in the manipulated masked image and normalizing the amount of area with unreacted polysilicon to the total gate area in the mask image to produce a fraction of unreacted polysilicon. An oxidizing solution composition of ammonium hydroxide and hydrogen peroxide, and an etching solution composition of hydrochloric acid, nitric acid and ethylene glycol are claimed.

DETAILED DESCRIPTION

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide a full understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The need for a method of measuring a fraction of unreacted polycrystalline silicon (polysilicon) in an integrated circuit (IC) with fully silicided (FUSI) gates on a statistically significant sample is addressed by the instant invention, which provides a method of deprocessing an IC in a novel manner to expose any unreacted polysilicon, acquiring an image of a statistically significant sample region using scanning electron microscopy (SEM), generating a mask image from the SEM sample image which identifies all gate regions in the SEM sample image, applying the mask image to the SEM sample image to produce a masked image of gate regions with unreacted polysilicon, manipulating the masked image to facilitate quantification of the gate regions with unreacted polysilicon, measuring the amount of area with unreacted polysilicon in the manipulated masked image and normalizing the amount of area with unreacted polysilicon to the total gate area in the mask image to produce a computation of a fraction of unreacted polysilicon.

Figure 1:
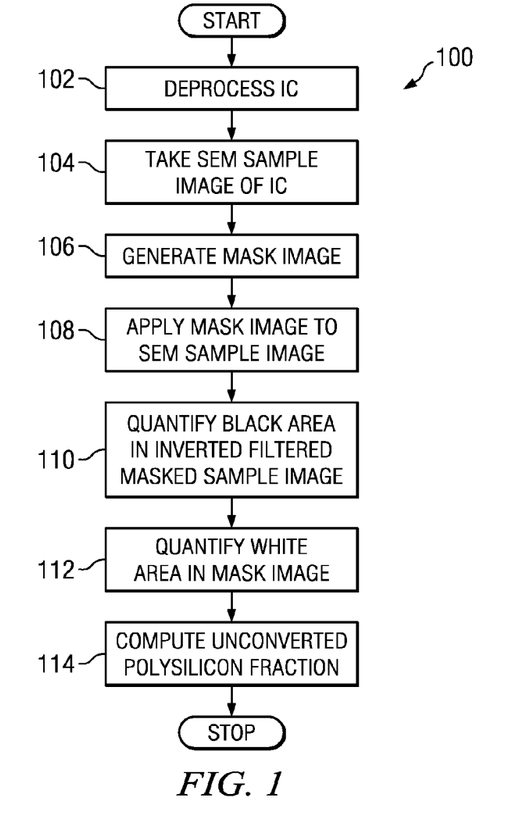
FIG. 1 is a flow chart of the inventive method of measuring the fraction of unreacted polysilicon in an IC.

FIG. 1 is a flow chart (100) of the inventive method of measuring the fraction of unreacted polysilicon in an IC. The first step (102) is to deprocess a portion or all of the IC such that all material around the unreacted polysilicon is removed, without disturbing underlying layers. The second step (104) is to acquire a top-down SEM sample image of a statistically significant sample region of the IC, which includes gate regions, and includes regions of unreacted polysilicon, if present in the gate regions. The third step (106) is to generate a mask image from the sample image, by a novel method of manipulating the contrast of the sample image and converting non-gate regions to black using automated techniques, such that gate regions of the sample image are reproduced as transparent regions in the mask image. The fourth step (108) is to apply the mask image to the sample image, producing a masked sample image in which only gate regions contain any image content, including unreacted polysilicon regions, and manipulate the masked sample image to generate an image of the unreacted polysilicon as black regions on a white background. The fifth step (110) is to quantify the amount of black area in the unreacted polysilicon image, which is proportional to the amount of unreacted polysilicon in the sample region of the IC. The sixth step (112) is to quantify the amount of transparent area in the mask image, which is proportional to the total amount of gate area in the sample region of the IC. The seventh step (114) is to divide the quantity of black area in the inverted filtered masked sample image by the quantity of white area in the mask image to produce a computation of the fraction of unreacted polysilicon in the gate region of the IC.

Figure 2:
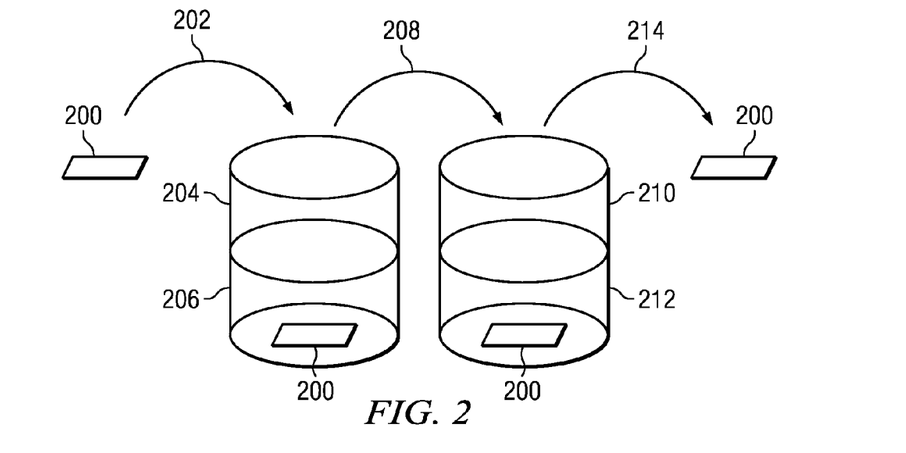
FIG. 2 depicts novel steps of the IC deprocessing operation noted in step (102) of the flowchart in FIG. 1.

FIG. 2 depicts novel steps of the IC deprocessing operation noted in step (102) of the flowchart in FIG. 1. The IC (200) may be in the form of a complete wafer or IC substrate, or a portion of a wafer or IC substrate. It is within the scope of this invention to deprocess a portion of the IC. The IC (200) is prepared so that material overlying gates is removed in a manner that does not disturb gate sidewall spacer material or layers the gates, such as silicon. The IC (200) is transferred, as depicted schematically by the arrow (202), to an oxidizing process apparatus (204), in which the IC (200) is exposed to an oxidizing solution (206), which is substantially composed of a mixture of ammonium hydroxide (30% to 50% in $H_2O$) and hydrogen peroxide (25% to 35% in $H_2O$) in the ratio of 4 to 1, at a temperature between 110 C and 175 C, whereby 115 to 125 C is preferred, for 30 to 50 minutes. The effect of the oxidizing solution on the IC is to oxidize nickel in nickel silicide forming FUSI gates on the IC (200). It is within the scope of this invention to vary the concentration of the ammonium hydroxide, the concentration of the hydrogen peroxide, the ratio of ammonium hydroxide to hydrogen peroxide, the temperature of the oxidizing solution, and the oxidizing exposure time in a manner such that the nickel in the nickel silicide is oxidized. Furthermore, it is within the scope of this invention to add or substitute other alkaline chemicals, such as tetra-methyl ammonium hydroxide, for the ammonium hydroxide and other oxidizing chemicals, such as ozone in water, for the hydrogen peroxide in the oxidizing solution (206). It is also within the scope of the instant invention to apply additional means to accomplish oxidation of the nickel in the oxidizing solution (206), including adding ultrasonic acoustic energy, commonly called megasonic action, to the solution. The oxidizing process apparatus (204) may be any equipment for containing the oxidizing solution (206) and the IC (200), and for exposing the IC (200) to the oxidizing solution (206), for example, a beaker, a spray bottle and sample holder, a semiconductor wafer wet processing hood, or a semiconductor wafer chemical spray tool.

Still referring to FIG. 2, after the nickel in the nickel silicide is oxidized, the IC (200) is transferred, with an optional rinse process and an optional dry process, as depicted schematically by the arrow (208), to an etching process apparatus (210), in which the IC (200) is exposed to an etching solution (212), which is substantially a mixture of hydrochloric acid (40% to 60% in $H_2O$), nitric acid (60% to 80% in $H_2O$) and ethylene glycol, in the ratio of 8 to 1 to 2, at room temperature, commonly 20 to 28 C, for 40 to 80 minutes. The effect of the etching solution on the IC is to remove all nickel and silicon that formed nickel silicide on the IC (200) before deprocessing, without removing gate sidewall spacer material such as silicon dioxide or silicon nitride on lateral surfaces of gates on the IC (200). It is within the scope of this invention to vary the concentration of the hydrochloric acid, the concentration of the nitric acid, the ratio of hydrochloric acid to nitric acid to ethylene glycol, the temperature of the etching solution, and the etching exposure time in a manner such that the nickel in the nickel silicide is oxidized. Furthermore, it is within the scope of this invention to add or substitute other acidic chemicals, such as phosphoric acid, for the hydrochloric acid and nitric acid in the etching solution (202). It is also within the scope of the instant invention to apply additional means to accomplish etching of the nickel silicide in the etching solution (212), including adding ultrasonic acoustic energy, commonly called megasonic action, to the solution. The etching process apparatus (210) may be any equipment for containing the etching solution (212) and the IC (200), and for exposing the IC (200) to the etching solution (212), for example, a beaker, a spray bottle and sample holder, a semiconductor wafer wet acid processing hood, or a semiconductor wafer chemical spray tool.

Continuing to refer to FIG. 2, after the nickel silicide is removed from the IC (200) in the etching processing apparatus (210), the IC (200) is removed from the etching processing apparatus (210), as depicted schematically by the arrow (214), followed by a second optional rinse process and a second optional dry process.

Figure 3A:
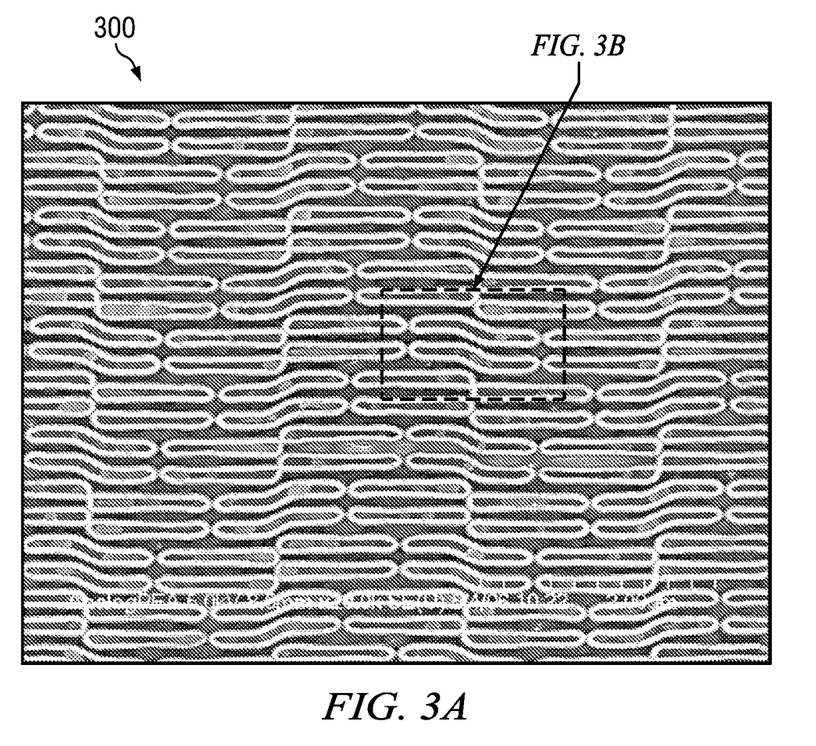
FIG. 3A and FIG. 3B are an SEM sample image of a sample region of an IC after deprocessing and an expanded portion of the SEM sample image, as called for in step (104) of the flowchart in FIG. 1.
Figure 3B:
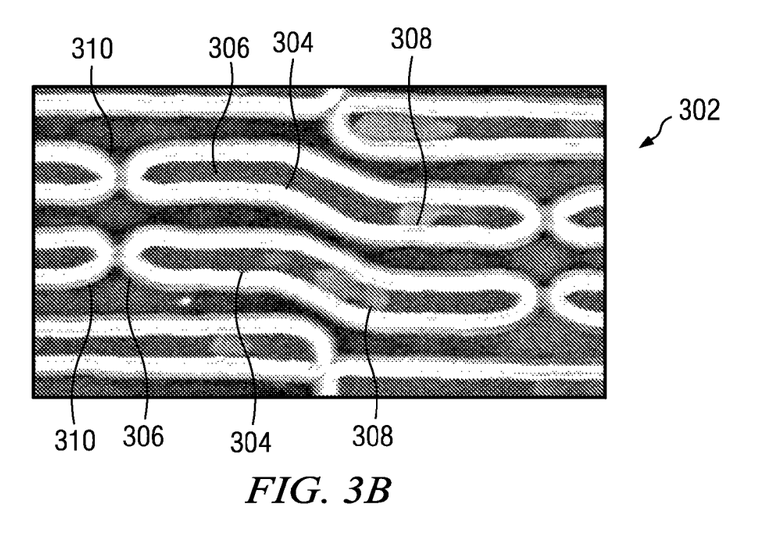

FIG. 3A and FIG. 3B are an SEM sample image of a sample region of an IC after deprocessing and an expanded portion of the SEM sample image, as called for in step (104) of the flowchart in FIG. 1. The SEM sample image is acquired in a preferred embodiment by backscattered electron imaging using a 5 kV beam and image contrast is optimized using known methods. The SEM sample image (300) shows multiple gate areas that have been deprocessed. An expanded image portion (302) of the SEM sample image (300) shows two gate areas (304) that have been deprocessed. Gate areas with no unreacted polysilicon appear black in the SEM sample image (300) and the expanded image portion (302). Gate sidewall spacer areas (306) appear white in the SEM sample image (300) and the expanded image portion (302). Unreacted polysilicon areas (308) appear gray in the SEM sample image (300) and the expanded image portion (302). Non-gate areas (310), which are defined for the purposes of this disclosure to mean areas other than gate areas or gate sidewall spacer areas, appear black in the SEM sample image (300) and the expanded image portion (302). It is within the scope of the instant invention to generate a sample image by other means that clearly distinguish unreacted polysilicon areas, clear gate areas, gate sidewall spacer areas and non-gate areas.

Figure 4A:
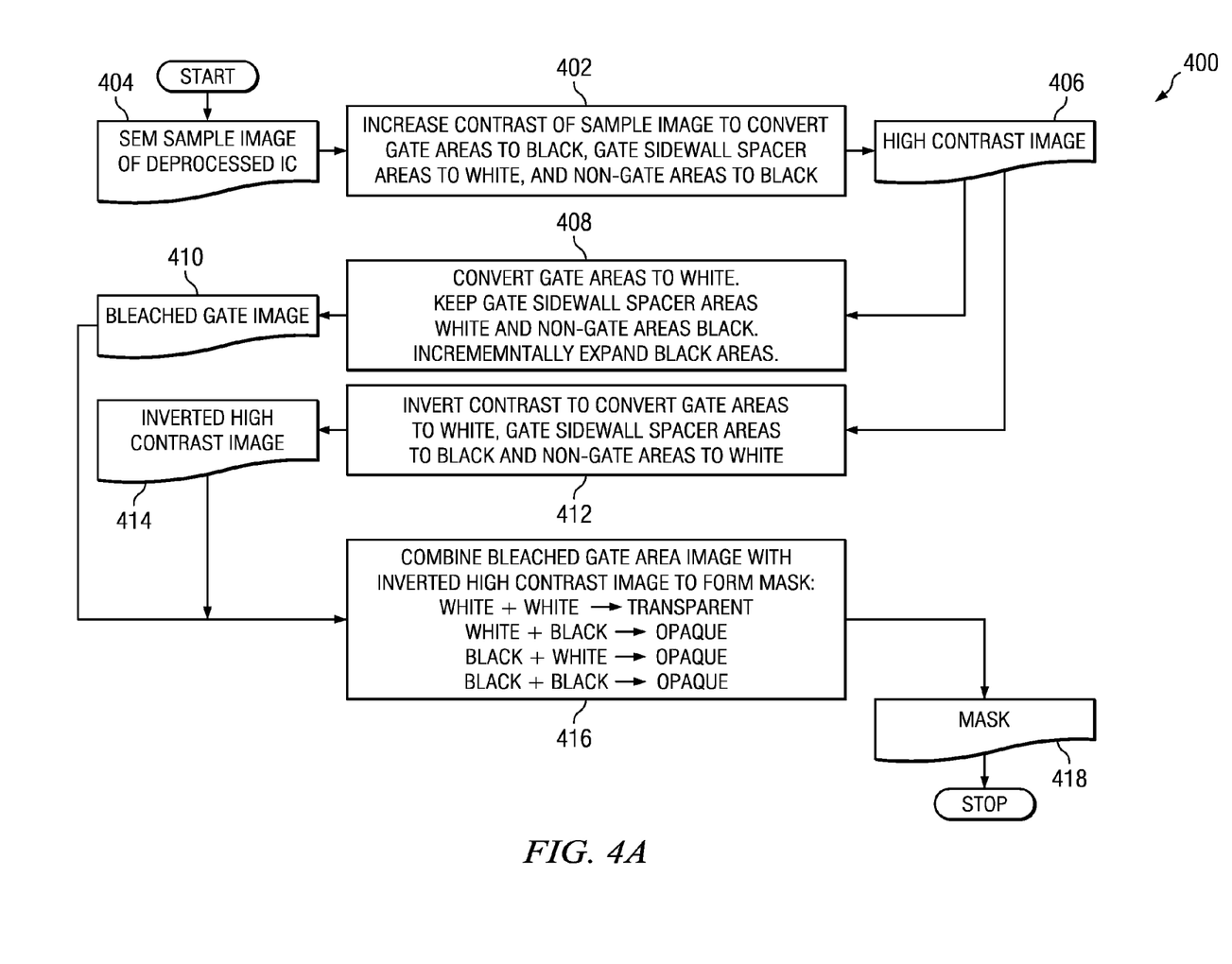
FIG. 4A is a flowchart (400) of the process for generating an mask image, as called for in step (106) of the flowchart in FIG. 1.
Figure 4B:
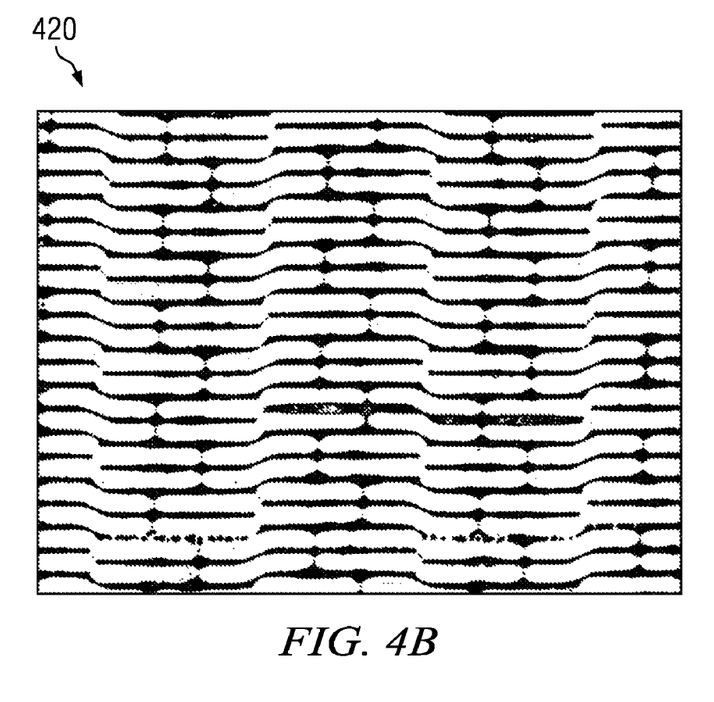
FIG. 4B through FIG. 4D are images of successive steps in the process of generating the mask image.
Figure 4C:
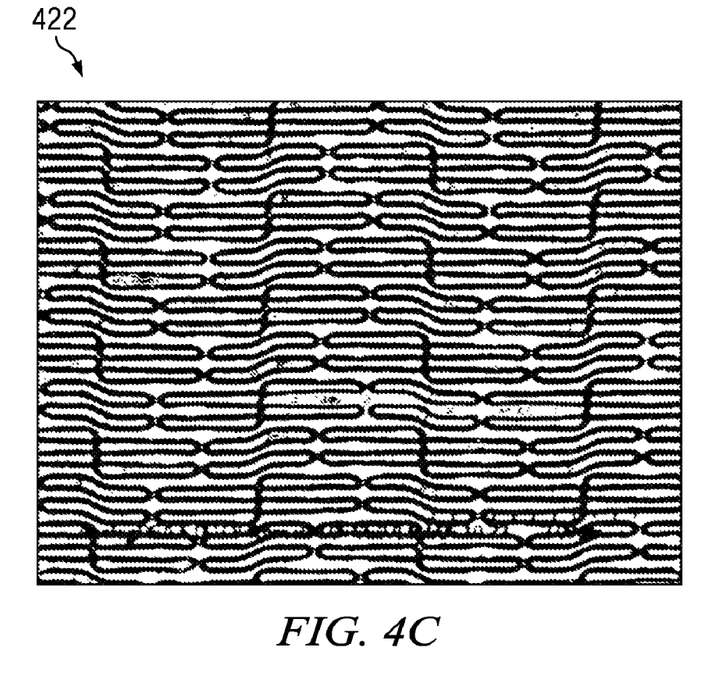
Figure 4D:
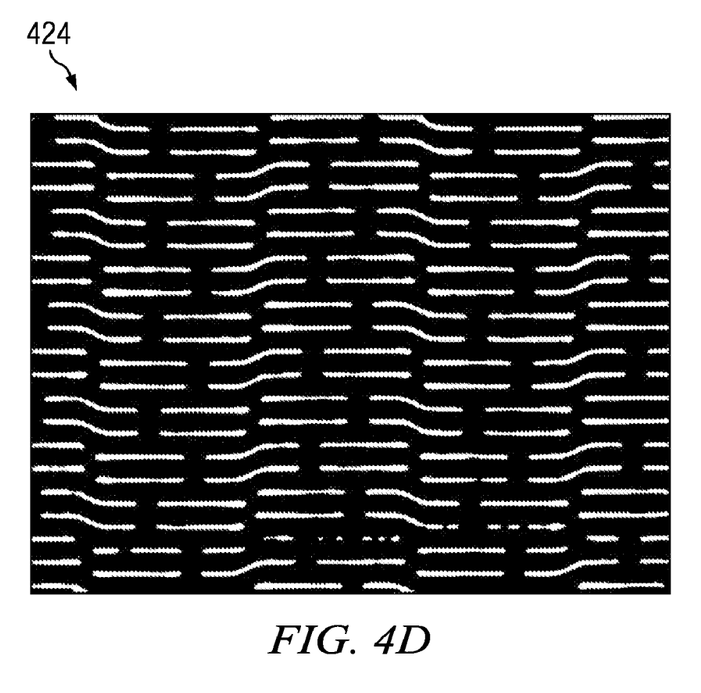

FIG. 4A is a flowchart (400) of the process for generating an mask image, as called for in step (106) of the flowchart in FIG. 1. FIG. 4B through FIG. 4D are images of successive steps in the process of generating the mask image. Referring to FIG. 4A, the process of generating the mask image starts with step (402), which is to start with the SEM sample image as input (404) and increase a contrast of the SEM sample image to convert the gate areas to black, gate sidewall spacer areas to white, and the non-gate areas to black, to form a high contrast image (406) as output.

Still referring FIG. 4A, the next step in generating the mask image is step (408), which is to convert the gate areas in the high contrast image (406) to white while keeping the gate sidewall spacer areas in the high contrast image (406) white and the non-gate areas in the high contrast image (406) black. The black areas are then incrementally expanded at their borders. The output of this step is a bleached gate image (410). FIG. 4B shows the bleached gate image (420) that results from this step.

Referring once again to FIG. 4A, the next step in generating the mask image is step (412), which is to start with the high contrast image (406) and invert the contrast, so that gates areas are white, gate sidewall spacer areas are black, and non-gate areas are white. The output of this step in an inverted high contrast image (414). FIG. 4C shows the inverted high contrast image (422) that results from this step.

Referring once again to FIG. 4A, the last step in generating the mask image is step (416), which is to combine the inverted high contrast image (414) with the bleached gate image (410) to form the mask image (418), according to the following procedure:

- Regions in the mask image (418) corresponding to white regions in the inverted high contrast image (414) and white regions in the bleached gate image (410) are transparent.
- Regions in the mask image (418) corresponding to white regions in the inverted high contrast image (414) and black regions in the bleached gate image (410) are opaque.
- Regions in the mask image (418) corresponding to black regions in the inverted high contrast image (414) and white regions in the bleached gate image (410) are opaque.
- Regions in the mask image (418) corresponding to black regions in the inverted high contrast image (414) and black regions in the bleached gate image (410) are opaque.

FIG. 4D shows the mask image (424) that results from this step. Transparent regions in the mask image appear as white in (424) while opaque regions in the mask image appear as black in (424).

In a preferred embodiment, the steps described in reference to FIG. 4A through FIG. 4D may be performed using a computing apparatus such as a general purpose computer or a dedicated image processing apparatus. In another embodiment, the steps described in reference to FIG. 4A through FIG. 4D may be performed by physically manipulating a printout of the SEM sample image. In a further embodiment, the steps described in reference to FIG. 4A through FIG. 4D may be performed by a combination of using a computing apparatus and physically manipulating a printout of the SEM sample image.

Figure 5A:
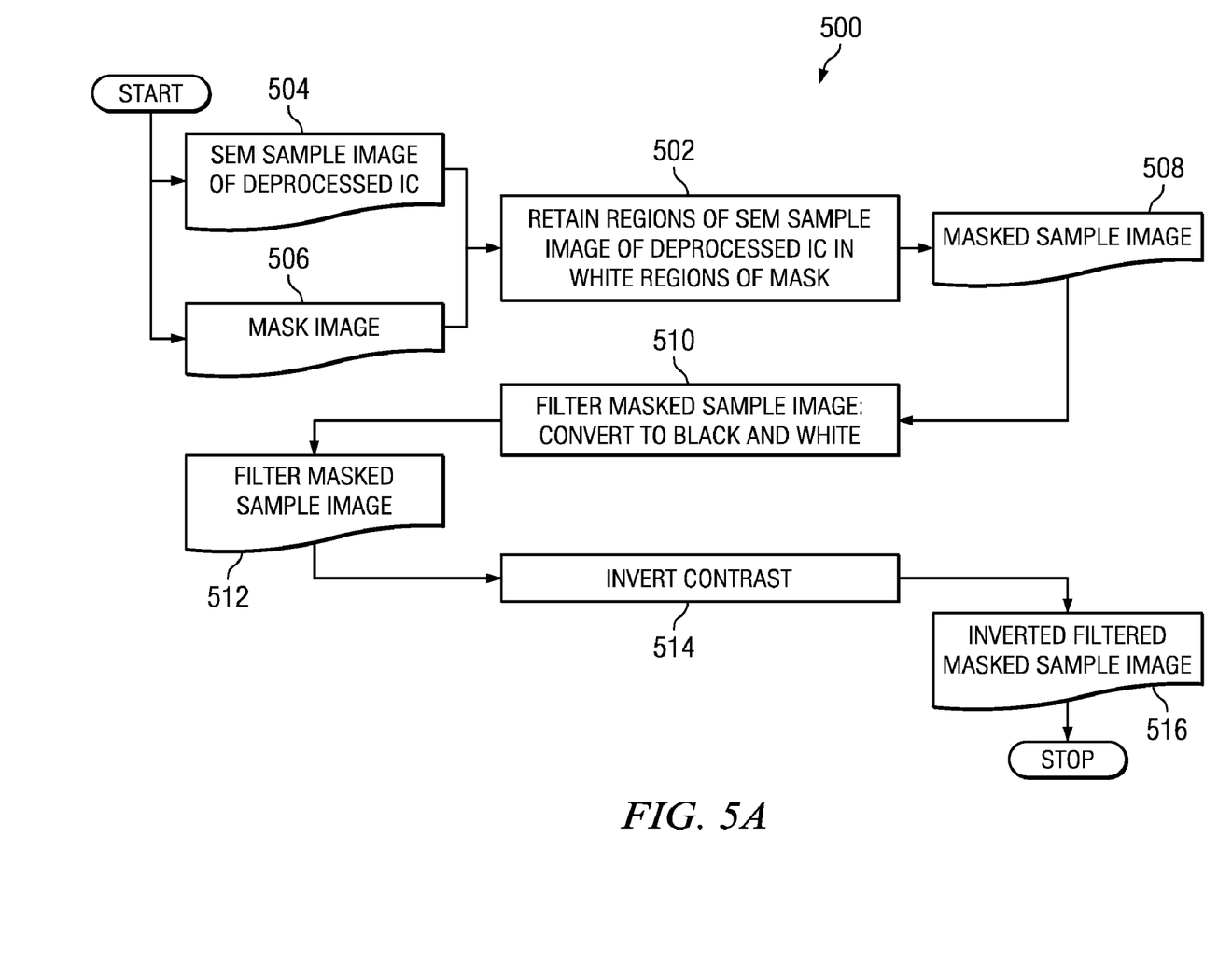
FIG. 5A is a flowchart (500) of a process for applying the mask image to the SEM sample image, as called for in step (108) of the flowchart (100) in FIG. 1.
Figure 5B:
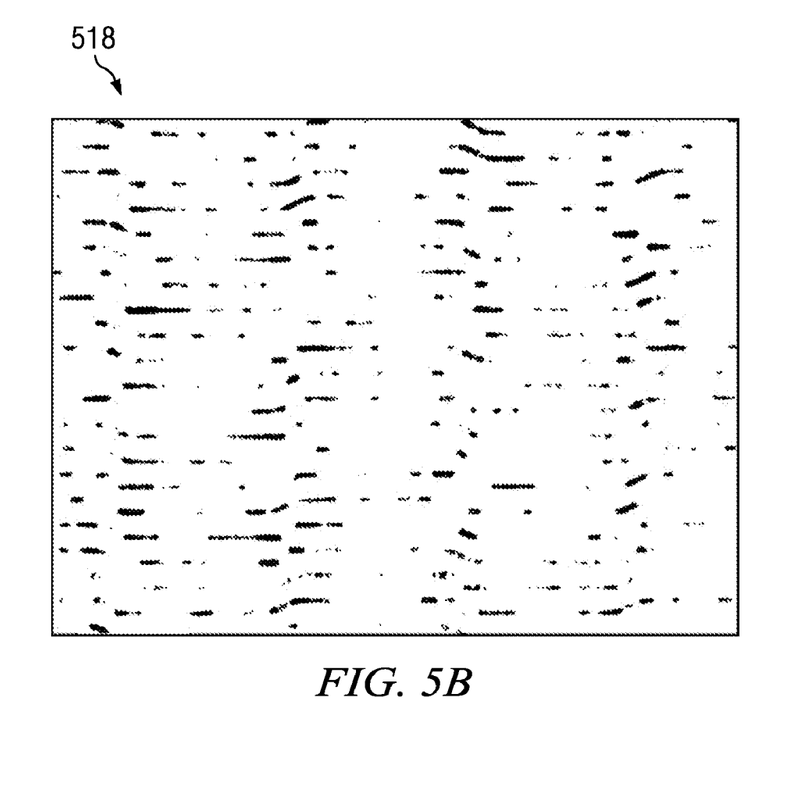
FIG. 5B is an image of unreacted polysilicon as black regions on a white background, produced by the process of the flowchart (500) in FIG. 5A.

FIG. 5A is a flowchart (500) of a process for applying the mask image (424) of FIG. 4 to the SEM sample image, as called for in step (108) of the flowchart (100) in FIG. 1. FIG. 5B is an image of unreacted polysilicon as black regions on a white background, produced by the process of the flowchart (500) in FIG. 5A. Referring to FIG. 5A, the process of applying the mask image (424) of FIG. 4 to the SEM sample image starts with step (502), which is to start with the SEM sample image (504) and retain image information only from regions corresponding to transparent regions in the mask image (506) which is the mask image (424) of FIG. 4, to produce a masked sample image (508). Regions in the masked sample image (508) corresponding to opaque regions in the mask image are filled in with black.

Still referring to FIG. 5A, the next step in applying the mask image (506) to the SEM sample image is step (510), which is to filter the masked sample image (508) by increasing the contrast of the masked sample image (508), resulting in regions corresponding to unreacted polysilicon becoming white, and gate regions with no unreacted polysilicon, as well as regions outside the gate areas, becoming or remaining black, to produce a filtered masked sample image (512) which contains only regions of white, corresponding to unreacted polysilicon, on a black background.

Continuing to refer to FIG. 5A, the last step in applying the mask image (506) to the SEM sample image is step (514), which is to optionally invert a contrast of the filtered masked sample image (512) to produce a black and white inverted filtered masked sample image (516) in which regions corresponding to unreacted polysilicon in the original SEM sample image are black on a white background, shown in FIG. 5B as image (518). Inverting the contrast of the filtered masked sample image (512) is advantageous because the inverted filtered masked sample image (516) is easier to analyze visually.

In a preferred embodiment, the steps described in reference to FIG. 5A and FIG. 5B may be performed using a computing apparatus such as a general purpose computer or a dedicated image processing apparatus. In another embodiment, the steps described in reference to FIG. 5A and FIG. 5B may be performed by physically manipulating a printout of the SEM sample image. In a further embodiment, the steps described in reference to FIG. 5A and FIG. 5B may be performed by a combination of using a computing apparatus and physically manipulating a printout of the SEM sample image.

The step of quantifying the black area in the inverted filtered masked sample image, as called for in step (110) of the flowchart (100) in FIG. 1, may be performed in a preferred embodiment using a computing apparatus such as a general purpose computer or a dedicated image processing apparatus. In another embodiment, quantifying the black area in the inverted filtered masked sample image may be performed by visual analysis of a printout of the inverted filtered masked sample image. In a further embodiment, quantifying the black area in the inverted filtered masked sample image may be performed by a combination of using a computing apparatus and visual analysis of a printout of the inverted filtered masked sample image. The result of quantifying the black area in the inverted filtered masked sample image is a number corresponding to the amount of unreacted polysilicon in the original SEM sample image (300) in FIG. 3A, for example the number of black pixels in the inverted filtered masked sample image.

The step of quantifying the transparent area in the mask image (506), as called for in step (112) of the flowchart (100) in FIG. 1, may be performed in a preferred embodiment using a computing apparatus such as a general purpose computer or a dedicated image processing apparatus. In another embodiment, quantifying the transparent area in the mask image (506) may be performed by visual analysis of a printout of the mask image (506). In a further embodiment, quantifying the white area in the mask image (506) may be performed by a combination of using a computing apparatus and visual analysis of a printout of the mask image (506). The result of quantifying the transparent area in the mask image (506) is a number corresponding to the amount of gate area in the original SEM sample image (300) in FIG. 3A, for example the number of transparent pixels in the mask image (506).

The step of computing the unreacted polysilicon fraction, as called for in step (114) of the flowchart (100) in FIG. 1, may be performed, using the amount of black area in the inverted filtered masked sample image from execution of step (110) in the flowchart (100) in FIG. 1, and the amount of transparent area in the mask image (506) from execution of step (112) in the flowchart (100) in FIG. 1, according to the following expression: unreacted polysilicon fraction =(the amount of black area in the inverted filtered masked sample image) divided by (the amount of transparent area in the mask image (506)). The step of computing the unreacted polysilicon fraction may be in a preferred embodiment by a computing apparatus such as a general purpose computer. In other embodiments, the computation of the unreacted polysilicon fraction may be performed manually, or using a hand calculator, or any other means to perform the computation recited above.

It is within the scope of the instant invention to substitute other colors for black and white in the images described above, including exchanging black for white.

The procedure for measuring the first fraction of unreacted polysilicon, as described above in reference to FIG. 1, FIG. 2, FIG. 3A and FIG. 3B, FIG. 4A through FIG. 4D and FIG. 5A through FIG. 5B, is advantageous because it provides statistically significant sample in as little as 4 hours that can be used to characterize a nickel silicide process with less than 10 measurements. By comparison, hundreds of TEM samples would be required to provide a comparable characterization, with a corresponding higher cost and longer time delay.

In one embodiment, the procedure for measuring the first fraction of unreacted polysilicon may be used to compare different silicide formation processes. In an alternate embodiment, the procedure for measuring the first fraction of unreacted polysilicon may also be used to monitor production of ICs using fully silicided gates. Furthermore, the procedure for measuring the first fraction of unreacted polysilicon may be used to adjust the FUSI nickel silicide process to reduce a fraction of unreacted polysilicon on a second IC.

In a further embodiment, a FUSI nickel silicide process may be developed by the following process. A first IC may be produced using a first FUSI nickel silicide process. A first fraction of unreacted polysilicon may be measured on a sample of the first IC using the process described in the embodiments recited herein. Process parameters of the first FUSI nickel silicide process, such as a thickness of a deposited nickel layer, or silicide formation temperature and/or time, may be adjusted to generate a second FUSI nickel silicide process. This adjustment may be made based on the first fraction of unreacted polysilicon. A second IC may be formed using the second FUSI nickel silicide process. A first fraction of unreacted polysilicon may be measured on a sample of the second IC using the process described in the embodiments recited herein. The first fraction of unreacted polysilicon from the first IC may be compared to the first fraction of unreacted polysilicon from the second IC to allow selection of a preferred FUSI nickel silicide process.

What is claimed is:

1. A method for measuring a fraction of unreacted polycrystalline silicon (polysilicon) in a sample of an integrated circuit (IC) with fully silicided (FUSI) gates, comprising the steps of:
deprocessing said sample to remove nickel silicide, further comprising the steps of:
exposing said sample to an oxidizing solution such that nickel in said nickel silicide is oxidized; and
exposing said sample to an etching solution such that said nickel silicide is removed;
generating an SEM sample image of said sample by scanning electron microscopy (SEM), such that said SEM sample image includes gate areas;
acquiring a mask image from said SEM sample image in which said gate areas are easily distinguished from non-gate areas;
applying said mask image to said SEM sample image to produce a masked sample image in which image information from said gate areas in said SEM sample image is included in said masked sample image and information from said non-gate areas in said SEM sample image is not included in said masked sample image;
filtering and inverting a contrast of said masked sample image to produce an inverted filtered masked sample image in which regions corresponding to unreacted polysilicon are assigned a first attribute and all other regions are assigned a second attribute; and
computing said fraction of unreacted polysilicon by a process further comprising the steps of:
quantifying an area in said inverted filtered masked sample image with said first attribute;
quantifying an area in said mask image of said gate areas; and
dividing said area with said first attribute by said area of said gate areas.

2. The method of claim 1, in which said oxidizing solution is substantially a mixture of ammonium hydroxide (30% to 50% in $H_2O$) and hydrogen peroxide (25% to 35% in $H_2O$) in the ratio of 4 to 1, at a temperature of 115 to 125 C.

3. The method of claim 2, in which said etching solution is substantially a hydrochloric acid (40% to 60% in $H_2O$), nitric acid (60% to 80% in $H_2O$) and ethylene glycol, in the ratio of 8 to 1 to 2, at a temperature of 20 to 28 C.

4. The method of claim 3, in which said step of generating a mask image further comprises the steps of:
increasing a contrast of said SEM sample image to produce a high contrast image in which gate regions appear black, gate sidewall areas appear white and non-gate areas appear black;
converting gate regions in said high contrast image to white and incrementally expanding black regions to produce a bleached gate image;
inverting a contrast in said high contrast image to produce an inverted high contrast image;
combining said inverted high contrast image with said bleached gate image to produce a mask image, such that:
regions in said mask image corresponding to white regions in said inverted high contrast image and white regions in said bleached gate image are transparent;
regions in said mask image corresponding to white regions in said inverted high contrast image and black regions in said bleached gate image are opaque;
regions in said mask image corresponding to black regions in said inverted high contrast image and white regions in said bleached gate image are opaque; and
regions in said mask image corresponding to black regions in said inverted high contrast image and black regions in said bleached gate image are opaque.

5. The method of claim 4, in which said step of filtering and inverting contrast of said masked sample image to produce an inverted filtered masked sample image further comprises the steps of:
increasing a contrast of said masked sample image to produce a filtered masked sample image such that regions corresponding to unreacted polysilicon in said SEM sample image are white and regions corresponding to gate regions in said SEM sample image with no unreacted polysilicon are black; and
inverting a contrast of said filtered masked sample image to produce an inverted filtered masked sample image in which said regions corresponding to unreacted polysilicon in said SEM sample image are black on a white background.

6. The method of claim 5, in which said steps of generating a mask image, applying said mask image to said SEM sample image, and filtering and inverting a contrast of said masked sample image are performed on a general purpose computer.

7. A method for fabricating an IC, comprising the steps of:
forming gates of metal oxide semiconductor (MOS) transistors on a first IC using a fully silicided (FUSI) nickel silicide process;
deprocessing a sample of said first IC to remove nickel silicide in said gates, further comprising the steps of:
exposing said sample to an oxidizing solution such that nickel in said nickel silicide is oxidized; and
exposing said sample to an etching solution such that said nickel silicide is removed;
acquiring an SEM sample image of said sample by scanning electron microscopy (SEM);
generating a mask image from said SEM sample image in which gate areas are easily distinguished from non-gate areas;
applying said mask image to said SEM sample image to produce a masked sample image in which image information only from regions corresponding to said gate areas in said mask image;
filtering and inverting a contrast of said masked sample image to produce an inverted filtered masked sample image in which regions corresponding to unreacted polysilicon are assigned a first attribute and all other regions are assigned a second attribute;
computing a fraction of unreacted polysilicon by a process further comprising the steps of:
quantifying an area in said inverted filtered masked sample image with said first attribute;
quantifying an area in said mask image of said gate areas; and
dividing said area with said first attribute by said area of said gate areas;
and
adjusting said FUSI nickel silicide process using said fraction of unreacted polysilicon on said first IC to reduce a fraction of unreacted polysilicon on a second IC.

8. The method of claim 7, in which said oxidizing solution is substantially a mixture of ammonium hydroxide (30% to 50% in $H_2O$) and hydrogen peroxide (25% to 35% in $H_2O$) in the ratio of 4 to 1, at a temperature of 115 to 125 C.

9. The method of claim 8, in which said etching solution is substantially a hydrochloric acid (40% to 60% in $H_2O$), nitric acid (60% to 80% in $H_2O$) and ethylene glycol, in the ratio of 8 to 1 to 2, at a temperature of 20 to 28 C.

10. The method of claim 9, in which said step of generating a mask image further comprises the steps of:
increasing a contrast of said SEM sample image to produce a high contrast image in which gate regions appear black, gate sidewall areas appear white and non-gate areas appear black;
converting gate regions in said high contrast image to white and incrementally expanding black regions to produce a bleached gate image;
inverting a contrast in said high contrast image to produce an inverted high contrast image;
combining said inverted high contrast image with said bleached gate image to produce a mask image, such that:
regions in said mask image corresponding to white regions in said inverted high contrast image and white regions in said bleached gate image are transparent;
regions in said mask image corresponding to white regions in said inverted high contrast image and black regions in said bleached gate image are opaque;
regions in said mask image corresponding to black regions in said inverted high contrast image and white regions in said bleached gate image are opaque; and
regions in said mask image corresponding to black regions in said inverted high contrast image and black regions in said bleached gate image are opaque.

11. The method of claim 10, in which said step of filtering and inverting contrast of said masked sample image to produce an inverted filtered masked sample image further comprises the steps of:
increasing a contrast of said masked sample image to produce a filtered masked sample image such that regions corresponding to unreacted polysilicon in said SEM sample image become white and regions corresponding to gate regions in said SEM sample image with no unreacted polysilicon become black; and
inverting a contrast of said filtered masked sample image to produce an inverted filtered masked sample image in which said regions corresponding to unreacted polysilicon in said SEM sample image are black on a white background.

12. The method of claim 11, in which said steps of generating a mask image, applying said mask image to said SEM sample image, and filtering and inverting a contrast of said masked sample image are performed on a general purpose computer.

13. A method for developing a FUSI nickel silicide process, comprising the step of:
providing a first IC;
forming a first set of gates of metal oxide semiconductor (MOS) transistors on said first IC using a first fully silicided (FUSI) nickel silicide process;
deprocessing a first sample of said first IC to remove a first instance of nickel silicide in said first set of gates, further comprising the steps of:
exposing said first sample to an oxidizing solution such that nickel in said first instance of nickel silicide is oxidized; and
exposing said first sample to an etching solution such that said first instance of nickel silicide is removed;
acquiring a first SEM sample image of said first sample by scanning electron microscopy (SEM);
generating a first mask image from said first SEM sample image in which gate areas are easily distinguished from non-gate areas;
applying said first mask image to said first SEM sample image to produce a first masked sample image in which image information only from regions corresponding to said gate areas in said first mask image;
filtering and inverting a contrast of said first masked sample image to produce a first inverted filtered masked sample image in which regions corresponding to unreacted polysilicon are assigned a first attribute and all other regions are assigned a second attribute;
computing a first fraction of unreacted polysilicon by a process further comprising the steps of:
quantifying a first area in said first inverted filtered masked sample image with said first attribute;
quantifying a first area in said first mask image of said gate areas; and
dividing said first area with said first attribute by said first area of said gate areas;
providing a second IC;
forming a second set of gates of metal oxide semiconductor (MOS) transistors on said second IC using a second fully silicided (FUSI) nickel silicide process;
deprocessing a second sample of said second IC to remove a second instance of nickel silicide in said second set of gates, further comprising the steps of:

exposing said second sample to an oxidizing solution such that nickel in said second instance of nickel silicide is oxidized; and exposing said second sample to an etching solution such that said second instance of nickel silicide is removed;

acquiring a second SEM sample image of said second sample by scanning electron microscopy (SEM);

generating a second mask image from said second SEM sample image in which gate areas are easily distinguished from non-gate areas;

applying said second mask image to said second SEM sample image to produce a second masked sample image in which image information only from regions corresponding to said gate areas in said second mask image;

filtering and inverting a contrast of said second masked sample image to produce a second inverted filtered masked sample image in which regions corresponding to unreacted polysilicon are assigned said first attribute and all other regions are assigned said second attribute;

computing a second fraction of unreacted polysilicon by a process further comprising the steps of:
  quantifying a second area in said second inverted filtered masked sample image with said first attribute;
  quantifying a second area in said second mask image of said gate areas; and
  dividing said second area with said first attribute by said second area of said gate areas;

and selecting a FUSI nickel silicide process based on said first fraction of unreacted polysilicon and said second fraction of unreacted polysilicon.

14. The method of claim 13, in which said oxidizing solution is substantially a mixture of ammonium hydroxide (30% to 50% in $H_2O$) and hydrogen peroxide (25% to 35% in $H_2O$) in the ratio of 4 to 1, at a temperature of 115 to 125 C.

15. The method of claim 14, in which said etching solution is substantially a hydrochloric acid (40% to 60% in $H_2O$), nitric acid (60% to 80% in $H_2O$) and ethylene glycol, in the ratio of 8 to 1 to 2, at a temperature of 20 to 28 C.

16. The method of claim 15, in which said steps of generating a first mask image and generating a second mask image further comprise the steps of:
  increasing a contrast of said SEM sample image to produce a high contrast image in which gate regions appear black, gate sidewall areas appear white and non-gate areas appear black;
  converting gate regions in said high contrast image to white and incrementally expanding black regions to produce a bleached gate image;
  inverting a contrast in said high contrast image to produce an inverted high contrast image;
  combining said inverted high contrast image with said bleached gate image to produce a mask image, such that:
    regions in said mask image corresponding to white regions in said inverted high contrast image and white regions in said bleached gate image are transparent;
    regions in said mask image corresponding to white regions in said inverted high contrast image and black regions in said bleached gate image are opaque;
    regions in said mask image corresponding to black regions in said inverted high contrast image and white regions in said bleached gate image are opaque; and
    regions in said mask image corresponding to black regions in said inverted high contrast image and black regions in said bleached gate image are opaque.

17. The method of claim 16, in which said steps of filtering and inverting contrast of said first masked sample image and further filtering and inverting contrast of said second masked sample image comprise the steps of:
  increasing contrasts of said first and second masked sample images to produce first and second filtered masked sample images such that regions corresponding to unreacted polysilicon in said first and second SEM sample images, respectively, become white and regions corresponding to gate regions in said first and second SEM sample images with no unreacted polysilicon become black; and
  inverting contrasts of said first and second filtered masked sample images to produce first and second inverted filtered masked sample images in which said regions corresponding to unreacted polysilicon in said first and second SEM sample images, respectively, are black on a white background.

18. The method of claim 17, in which said steps of generating first and second mask images, applying said first and second mask images to said first and second SEM sample images, and filtering and inverting contrasts of said first and second masked sample images are performed on a general purpose computer.

* * * * *